(12) United States Patent
Mescher et al.

(10) Patent No.: US 9,046,192 B2
(45) Date of Patent: Jun. 2, 2015

(54) MEMBRANE-BASED FLUID CONTROL IN MICROFLUIDIC DEVICES

(75) Inventors: Mark J. Mescher, West Newton, MA (US); Jason O. Fiering, Boston, MA (US); Erin E. Swan, Swampscott, MA (US)

(73) Assignee: The Charles Stark Draper Laboratory, Inc., Cambridge, MA (US)

( * ) Notice: Subject to any disclaimer, the term of this patent is extended or adjusted under 35 U.S.C. 154(b) by 1556 days.

(21) Appl. No.: 12/023,653

(22) Filed: Jan. 31, 2008

(65) Prior Publication Data

US 2008/0249510 A1    Oct. 9, 2008

Related U.S. Application Data

(60) Provisional application No. 60/898,822, filed on Jan. 31, 2007, provisional application No. 60/898,821, filed on Jan. 31, 2007.

(51) Int. Cl.

| F16K 99/00 | (2006.01) |
|---|---|
| A61M 5/142 | (2006.01) |
| G05D 7/01 | (2006.01) |
| A61M 5/14 | (2006.01) |
| A61M 5/168 | (2006.01) |

(52) U.S. Cl.
CPC ........ *F16K 99/0001* (2013.01); *A61M 5/14276* (2013.01); *F16K 99/0015* (2013.01); *F16K 99/0034* (2013.01); *F16K 99/0042* (2013.01); *F16K 99/0055* (2013.01); *G05D 7/012* (2013.01); *A61M 5/141* (2013.01); *A61M 5/16809* (2013.01); *A61M 5/16813* (2013.01); *A61M 2205/0244* (2013.01); *A61M 2206/22* (2013.01); *F16K 2099/0076* (2013.01); *F16K 2099/008* (2013.01); *F16K 2099/0088* (2013.01)

(58) Field of Classification Search
USPC ........... 417/313, 540, 543; 138/26, 46; 251/7, 251/8, 4, 331
See application file for complete search history.

(56) References Cited

U.S. PATENT DOCUMENTS

| 3,386,469 | A | * | 6/1968 | Kelly ....................... 137/505.38 |
|---|---|---|---|---|
| 4,013,074 | A | | 3/1977 | Siposs |
| 4,034,759 | A | | 7/1977 | Haerr |
| 4,152,098 | A | | 5/1979 | Moody et al. |

(Continued)

FOREIGN PATENT DOCUMENTS

| EP | 1331019 | 7/2003 |
|---|---|---|
| WO | WO-95/20409 | 8/1995 |

(Continued)

OTHER PUBLICATIONS

B. Yang, et al. "Using Compliant Membranes for Dynamic Flow Stabilization in Microfluidic Systems," Proceedings of MEMS 2005, 706-709, 2005.

(Continued)

*Primary Examiner* — Christopher Bobish
(74) *Attorney, Agent, or Firm* — Edward A. Gordon; Foley & Lardner LLP

(57) ABSTRACT

A microfluidic device may include a substrate that defines a flow-control cavity and first and second channels in fluid communication with the flow-control cavity. A compliant membrane for regulating fluid flow through the flow-control cavity may surround at least a portion of the flow-control cavity.

25 Claims, 6 Drawing Sheets

(56) References Cited

U.S. PATENT DOCUMENTS

| | | | |
|---|---|---|---|
| 4,181,245 A | 1/1980 | Garrett et al. | |
| 4,487,603 A | 12/1984 | Harris | |
| 4,541,429 A | 9/1985 | Prosl et al. | |
| 4,548,240 A * | 10/1985 | Graham | 138/30 |
| 4,594,058 A | 6/1986 | Fischell | |
| 4,594,059 A * | 6/1986 | Becker | 417/439 |
| 4,604,090 A | 8/1986 | Reinicke | |
| 4,634,427 A | 1/1987 | Hannula et al. | |
| 4,824,073 A | 4/1989 | Zdeblick | |
| 4,858,883 A | 8/1989 | Webster | |
| 4,944,487 A | 7/1990 | Holtermann | |
| 5,065,978 A | 11/1991 | Albarda et al. | |
| 5,205,819 A | 4/1993 | Ross et al. | |
| 5,441,597 A | 8/1995 | Bonne et al. | |
| 5,476,446 A | 12/1995 | Arenburg | |
| 5,499,979 A | 3/1996 | Wong et al. | |
| 5,542,821 A | 8/1996 | Dugan | |
| 5,578,002 A | 11/1996 | Slettenmark | |
| 5,593,130 A | 1/1997 | Hansson et al. | |
| 5,643,207 A | 7/1997 | Rise | |
| 5,665,070 A | 9/1997 | McPhee | |
| 5,725,363 A | 3/1998 | Bustgens et al. | |
| 5,750,015 A | 5/1998 | Soane et al. | |
| 5,759,014 A | 6/1998 | Van Lintel et al. | |
| 5,770,029 A | 6/1998 | Nelson et al. | |
| 5,779,868 A | 7/1998 | Parce et al. | |
| 5,839,467 A * | 11/1998 | Saaski et al. | 137/501 |
| 5,858,188 A | 1/1999 | Soane et al. | |
| 5,858,195 A | 1/1999 | Ramsey | |
| 5,880,071 A | 3/1999 | Parce et al. | |
| 5,895,372 A | 4/1999 | Zenner et al. | |
| 5,938,904 A | 8/1999 | Bader et al. | |
| 5,954,079 A * | 9/1999 | Barth et al. | 137/13 |
| 5,958,203 A | 9/1999 | Parce et al. | |
| 5,962,081 A | 10/1999 | Ohman et al. | |
| 5,971,355 A | 10/1999 | Biegelsen et al. | |
| 5,972,187 A | 10/1999 | Parce et al. | |
| 5,989,399 A | 11/1999 | Chu et al. | |
| 5,989,402 A | 11/1999 | Chow et al. | |
| 5,993,634 A | 11/1999 | Simpson et al. | |
| 6,001,229 A | 12/1999 | Ramsey | |
| 6,007,690 A | 12/1999 | Nelson et al. | |
| 6,010,607 A | 1/2000 | Ramsey | |
| 6,010,608 A | 1/2000 | Ramsey | |
| 6,017,434 A | 1/2000 | Simpson et al. | |
| 6,033,191 A | 3/2000 | Kamper et al. | |
| 6,033,546 A | 3/2000 | Ramsey | |
| 6,033,628 A | 3/2000 | Kaltenbach et al. | |
| 6,042,709 A | 3/2000 | Parce et al. | |
| 6,042,710 A | 3/2000 | Dubrow | |
| 6,056,727 A * | 5/2000 | O'Neil | 604/183 |
| 6,068,010 A | 5/2000 | Reinicke | |
| 6,068,752 A | 5/2000 | Dubrow et al. | |
| 6,080,295 A | 6/2000 | Parce et al. | |
| 6,086,825 A | 7/2000 | Sundberg et al. | |
| 6,087,743 A | 7/2000 | Guckel et al. | |
| 6,093,296 A | 7/2000 | Soane et al. | |
| 6,103,199 A | 8/2000 | Bjornson et al. | |
| 6,110,343 A | 8/2000 | Ramsey et al. | |
| 6,113,768 A | 9/2000 | Fuhr et al. | |
| 6,120,666 A | 9/2000 | Jacobson et al. | |
| 6,123,316 A | 9/2000 | Biegelsen et al. | |
| 6,126,140 A | 10/2000 | Johnson et al. | |
| 6,126,804 A | 10/2000 | Andresen | |
| 6,132,579 A | 10/2000 | Edwards et al. | |
| 6,136,171 A | 10/2000 | Frazier et al. | |
| 6,153,073 A | 11/2000 | Dubrow et al. | |
| 6,176,991 B1 | 1/2001 | Nordman | |
| 6,193,866 B1 | 2/2001 | Bader et al. | |
| 6,198,966 B1 | 3/2001 | Heruth | |
| 6,207,031 B1 | 3/2001 | Adourian et al. | |
| 6,227,809 B1 | 5/2001 | Forster et al. | |
| 6,231,737 B1 | 5/2001 | Ramsey et al. | |
| 6,235,175 B1 | 5/2001 | Dubrow et al. | |
| 6,251,247 B1 | 6/2001 | Mitsuhashi et al. | |
| 6,254,754 B1 | 7/2001 | Ross et al. | |
| 6,261,430 B1 | 7/2001 | Yager et al. | |
| 6,261,431 B1 | 7/2001 | Mathies et al. | |
| 6,264,892 B1 | 7/2001 | Kaltenbach et al. | |
| 6,280,148 B1 | 8/2001 | Zengerle et al. | |
| 6,284,113 B1 | 9/2001 | Bjornson et al. | |
| 6,287,520 B1 | 9/2001 | Parce et al. | |
| 6,296,749 B1 | 10/2001 | Balch et al. | |
| 6,296,752 B1 | 10/2001 | McBride et al. | |
| 6,306,272 B1 | 10/2001 | Soane et al. | |
| 6,306,273 B1 | 10/2001 | Wainright et al. | |
| 6,341,758 B1 | 1/2002 | Shih et al. | |
| 6,342,142 B1 | 1/2002 | Ramsey | |
| 6,375,817 B1 | 4/2002 | Taylor et al. | |
| 6,386,780 B1 | 5/2002 | Brummernhenrich et al. | |
| 6,406,605 B1 | 6/2002 | Moles | |
| 6,413,400 B1 | 7/2002 | Soane et al. | |
| 6,423,198 B1 | 7/2002 | Manz et al. | |
| 6,440,102 B1 | 8/2002 | Arenberg et al. | |
| 6,440,284 B1 | 8/2002 | Dubrow | |
| 6,448,090 B1 | 9/2002 | McBride | |
| 6,458,259 B1 | 10/2002 | Parce et al. | |
| 6,482,177 B1 | 11/2002 | Leinders et al. | |
| 6,485,625 B1 | 11/2002 | Simpson et al. | |
| 6,527,003 B1 | 3/2003 | Webster et al. | |
| 6,540,895 B1 | 4/2003 | Spence et al. | |
| 6,547,942 B1 | 4/2003 | Parce et al. | |
| 6,561,224 B1 | 5/2003 | Cho | |
| 6,561,997 B1 | 5/2003 | Weitzel et al. | |
| 6,572,830 B1 | 6/2003 | Burdon et al. | |
| 6,578,816 B1 * | 6/2003 | Lille | 251/11 |
| 6,582,576 B1 | 6/2003 | Chow et al. | |
| 6,592,733 B1 | 7/2003 | Foley et al. | |
| 6,635,226 B1 | 10/2003 | Tso et al. | |
| 6,659,982 B2 | 12/2003 | Douglas et al. | |
| 6,660,147 B1 | 12/2003 | Woudenberg et al. | |
| 6,685,697 B1 | 2/2004 | Arenberg et al. | |
| 6,752,376 B1 | 6/2004 | Satou et al. | |
| 6,752,914 B1 | 6/2004 | Hassard et al. | |
| 6,764,060 B2 | 7/2004 | Fukano et al. | |
| 6,773,567 B1 | 8/2004 | Wolk | |
| 6,808,609 B1 | 10/2004 | Soane et al. | |
| 6,824,663 B1 | 11/2004 | Boone | |
| 6,827,831 B1 | 12/2004 | Chow et al. | |
| 6,830,558 B2 * | 12/2004 | Flaherty et al. | 604/67 |
| 6,929,030 B2 | 8/2005 | Unger et al. | |
| 6,929,239 B1 | 8/2005 | Colin et al. | |
| 6,945,116 B2 | 9/2005 | Xie et al. | |
| 6,948,918 B2 | 9/2005 | Hansen | |
| 6,986,365 B2 | 1/2006 | Henning et al. | |
| 7,033,148 B2 | 4/2006 | Bunner et al. | |
| 7,134,639 B2 | 11/2006 | Gilbert et al. | |
| 7,147,205 B1 | 12/2006 | Fischer et al. | |
| 7,192,001 B2 | 3/2007 | Wise et al. | |
| 7,232,109 B2 | 6/2007 | Driggs et al. | |
| 7,254,008 B2 | 8/2007 | Xie et al. | |
| 7,293,581 B2 | 11/2007 | Gilbert et al. | |
| 7,311,503 B2 | 12/2007 | Van Lintel et al. | |
| 2002/0048536 A1 | 4/2002 | Bergh et al. | |
| 2002/0098097 A1 | 7/2002 | Singh | |
| 2002/0127736 A1 | 9/2002 | Chou et al. | |
| 2002/0144738 A1 | 10/2002 | Unger et al. | |
| 2002/0166585 A1 | 11/2002 | O'Connor et al. | |
| 2002/0172969 A1 | 11/2002 | Burns et al. | |
| 2003/0071235 A1 | 4/2003 | Gamble et al. | |
| 2003/0127329 A1 | 7/2003 | DeVoe et al. | |
| 2003/0171738 A1 | 9/2003 | Konieczynski et al. | |
| 2003/0175947 A1 | 9/2003 | Liu et al. | |
| 2003/0196695 A1 | 10/2003 | O'Connor et al. | |
| 2003/0229336 A1 | 12/2003 | Jacobsen et al. | |
| 2004/0026461 A1 | 2/2004 | Bougamont et al. | |
| 2004/0036047 A1 | 2/2004 | Richter | |
| 2004/0053290 A1 | 3/2004 | Terbrueggen et al. | |
| 2004/0089357 A1 | 5/2004 | Dube et al. | |
| 2004/0127852 A1 | 7/2004 | Gray et al. | |
| 2004/0188648 A1 | 9/2004 | Xie et al. | |
| 2004/0249363 A1 * | 12/2004 | Burke et al. | 604/890.1 |
| 2005/0065584 A1 | 3/2005 | Schiff et al. | |
| 2005/0072946 A1 | 4/2005 | Studer et al. | |

(56) References Cited

U.S. PATENT DOCUMENTS

| | | | |
|---|---|---|---|
| 2005/0116798 | A1 | 6/2005 | Bintoro et al. |
| 2005/0131332 | A1 | 6/2005 | Kelly et al. |
| 2005/0238506 | A1 | 10/2005 | Mescher et al. |
| 2006/0030837 | A1 | 2/2006 | McKenna et al. |
| 2006/0287689 | A1 | 12/2006 | Debruyne |
| 2007/0200081 | A1 | 8/2007 | Elizarov et al. |
| 2007/0234785 | A1* | 10/2007 | Beerling et al. ............. 73/61.56 |
| 2008/0009836 | A1 | 1/2008 | Fiering et al. |

FOREIGN PATENT DOCUMENTS

| | | | | |
|---|---|---|---|---|
| WO | WO-99/38552 | | 8/1999 | |
| WO | WO-02/11703 | | 2/2002 | |
| WO | WO-03/034960 | | 5/2003 | |
| WO | WO-03/075984 | | 9/2003 | |
| WO | WO-03/099351 | | 12/2003 | |
| WO | WO-2005/072793 | | 8/2005 | |
| WO | WO 2006068263 | A1 * | 6/2006 | ............. F04B 11/00 |
| WO | WO-2007/024829 | | 3/2007 | |

OTHER PUBLICATIONS

D. B. Weibel, et al. "Torque-actuated Valves for Microfluidics" Analytical Chemistry 77(15), 4276-4733, Aug. 2005.

Brown et al. "Osmotic pump implant of drugs into the inner ear," Hearing Research 70 (1993) 167-172.

Cabuz et al. "MEMS-Based Flow Controller for Flow Cytometry" DARPA Contract MDA972-00-C-0029, 2 pgs.

Carvalho et al. "The Effect of Cochlesostomy and Intracochlear Infuction on Auditory Brain Stem Response Threshold in the Guinea Pig" The American Journal of Otology, 20:87-90 (1999).

Cousseau et al. "Improved Micro-Flow Regulator for Drug Delivery Systems" IEEE, 2001, 527-530.

Dube et al. "26.1: A Si-Based FPW Sensor Array System with Polymer Microfluidics Integrated on a PCB" IEEE (2002) 460-465.

Fitch et al. "Pressure-Based Mass Flow Control Using Thermopneumatically-Actuated Microvalves" In Proceedings, Sensors and Actuators Workshop, pp. 162-165 (Transducers Research Foundation, Cleveland, OH (1998).

Gantz et al. "Combing Acoustic and Electric Hearing" Department of Otolaryngology-Head and Neck Surgery and Department of Speech and Pathology, University of Iowa, pp. 1-18.

Hoffer et al. "Microdose Gentamicin Administration via the Round Window Microcatheter Results in Patients with Meniere's Disease" Annals New York Academy of Sciences, pp. 46-51.

International Search Report and Written Opinion for Application No. PCT/US05/002727 (11 pages), dated Apr. 28, 2005.

International Search Report and Written Opinion for Application No. PCT/US07/017817 (14 pages), dated Jan. 18, 2008.

International Search Report and Written Opinion for Application No. PCT/US08/001324 (21 pages), dated Sep. 30, 2008.

Kingma et al. "Chronic drug infusion into the scala tympani" Journal of Neuroscience Methods, 45 (1992) 127-134.

Kujawa et al. "A nicotinic-like receptor mediates suppression of distortion product otaoacoustic emissions by contralateral sound" Elsevier Science B.V., Hearing Research 74 (1994) 122-134.

Langer "Drugs on Target" Science (2001) vol. 293, 58-59.

Laryngologica "Round Window Gentamicin—Catheter—a New Therapeutic Tool in Menier's Disease" Charabi, Samih (2000) 120:1, 108-110.

Lehner et al. "A Totally Implantable Drug Delivery SYstem for Local Therapy of the Middle and Inner Ear" ENT—Ear Nose & Throat Journal (1997) vol. 76, No. 8, 567-570.

Lintel et al. "A Piezoelectric Micropump Based on Micromachining of Silicon" Sensors and Actuators, 15 (1988) 153-167.

Madou et al. "Exploitation of a Novel Artificial Muscle for Controlled Drug Delivery" Department of Chemistry and Materials Sciecne and Engineering, Ohio State Univ. 495-497.

Mescher et al. "Surface Mount Microfluidic Flow Regulator on a Polymer Substrate" 7th International Conference on Miniaturized Chemical and Biochemical Systems, Oct. 5-9, 2003, Squaw Valley, CA, 947-950.

Miller et al. "Neurotrophins Can Enhance Spiral Ganglion Cell Survival after Inner Hair Cell Loss" Int. J. Devl. Neuroscience, (1997) vol. 15, No. 4/5, pp. 631-643.

Paasche et al. "Technical Report: Modification of a Cohlear Implant Electrode for Drug Delivery to the Inner Ear" Ontology & Neurology (2003) 24:222-227.

Praetorius et al. "A Novel Microperfusion System for the Long-Term Local Supply of Drugs to the Inner Ear: Implantation and Function in the Rat Model" Audiol. Neurootol. (2001) 6:250-258.

Prieskorn et al. "technical report: chronic and acute intraochlear infusion in rodents" Elsevier, Hearing Research 140 (2000) 212-215.

Santini et al. "A controlled-release microchip" Nature, vol. 397, (1999) 335-338.

Schoendorf et al. "Continuous intratympanic infusion of gentamicin via a microcatheter in Meniere's disease" Otolaryngology-Head and Neck Surgery, vol. 124, No. 2 (2001) 203-207.

Shepherd et al. "A multichannel scala tympani electrode array incorporating a drug delivery system for chronic intracochlear infusion" Hearing Research 172 (2002) 92-98.

Smits "Piezoelectric Micropump with Three Valves Working Peristaltically" Sensors and Actuators, A21-A23 (1990) 206-206.

Sridhar et al. "Unique Postsynaptic Signaling at the Hair Cell Efferent Synapse Permits Calcium to Evoke Changes on Two Time Scales" The Journal of Neuroscience, (1997) 17(1):428-437.

Yu et al. "Responsive biomimetic hydrogel valve for microfluidics" Applied Physics Letters, vol. 78, No. 17 (2001) 2589-2591.

Zengerle et al. "A bidirectional silicon micropump" Sensors and Actuators A 50 (1995) 81-86.

* cited by examiner

US 9,046,192 B2

MEMBRANE-BASED FLUID CONTROL IN MICROFLUIDIC DEVICES

CROSS-REFERENCE TO RELATED APPLICATIONS

This application claims priority to and the benefit of U.S. provisional patent Application Nos. 60/898,821 and 60/898,822, both of which were filed on Jan. 31, 2007, the disclosures of which are hereby incorporated herein by reference in their entirety.

TECHNICAL FIELD

In various embodiments, the present invention relates to devices and methods for controlling fluid flow in microfluidic devices.

BACKGROUND

Existing drug-delivery technology is typically not appropriate for long-term programmable infusion into certain body parts, such as, for example, the inner ear. Known drug-delivery devices include external and implanted infusers, osmotic pumps, and erodible polymer-drug systems. These systems range from passive devices, which have a low level of predictability in their dispensing rates, to electronically-controlled rate dispensers, and finally to fully programmable infusers.

Device volumes range from approximately "pill" sized to over ten cubic inches, generally depending on their maximum dispensing volume and the sophistication of their control systems. Though small in volume, erodible polymer and porous membrane systems must typically be utilized to deliver a specific compound or, at best, a set of compounds with similar chemistry and transport properties. These devices are generally short to medium term delivery devices (i.e., less than approximately six weeks) with unalterable, non-constant delivery profiles. Existing osmotic pump-based delivery systems are similar in terms of device size and lifetime, and they too are typically only capable of fixed rate delivery. Other available devices may offer more sophisticated control, and may be effective for the treatment of disorders such as chronic pain, but these systems generally use macro-scale, conventionally fabricated pumps that are relatively large. As a result, they are generally only practical when implanted in subcutaneous tissue in the torso.

In some macro-scale systems (for example, pressure-regulation systems), bellows are used with fast valves to damp out rapid changes in pressure. Miniaturized bellows have been fabricated, but reliability and cost make them inappropriate for some applications. Other systems have used compliant tubing as a capacitive element. In such systems, as pressure increases, the tubing volume generally expands by an amount dependent on the tubing material and its dimensions. However, achieving appreciably large capacitance values using standard tubing requires a relatively large total tubing volume. Moreover, the tubing typically cannot have sufficiently thin walls to offer the values of capacitance desired within a small volume. Thus, relatively long and thick tubing sections are required, thereby increasing the total system volume of the injection system.

Small size is often important for many applications, particularly in implantable drug-delivery systems where both the trauma from the surgical implantation and foreign body response are reduced when the implant size is reduced. In addition, large tubing surface areas allow for significant vapor or gas permeation, which is detrimental to a system with low fluid volumes, particularly if they are not refilled. Integration of tubing as a capacitive element in a microfluidic system also requires connectors from the tubing to the other elements (e.g., pumps, valves, etc.). These connectors add to system volume and are a source of both leakage and dead volume. Yet another disadvantage in known microfluidic systems is their sensitivity to the tubing dimensions and mechanical properties, which may change over time.

In addition, a MEMS-based drug-delivery device may require a valve system for fluid control within the device. Exemplary valve systems known in the art are depicted in FIGS. 1A-2B. For example, FIGS. 1A and 1B depict a valve system 100 that includes a pair of four-way stopcock valves 120, 140. In this exemplary system 100, during filling of a fluidic manifold or loop 110, as depicted in FIG. 1A, one valve 120 typically connects a load reservoir (not shown) to the manifold 110 through a load reservoir connector 130, while another valve 140 vents the other end of the manifold 110 though a venting connector 150. As depicted in FIG. 1B, during manifold circulation in the direction indicated by the arrows 160, the two stopcock valves 120, 140 are rotated to join the input and output sections of the manifold or loop 110.

FIGS. 2A and 2B depict an exemplary rotary-type valve system 200. During loading, as depicted in FIG. 2A, a load reservoir connector 130 and an inlet 210 of the manifold 110 are connected through a valve 230, and an outlet 220 of the manifold 110 is vented through a venting connector 150. During circulation, as depicted in FIG. 2B, the manifold inlet 210 and outlet 220 may be connected to valve chambers within the rotary valve 230 and to a connector 240, external to the valve 230, which joins those valve chambers.

Unfortunately, the size of both the stopcock valves 120, 140 and rotary valves 230 is large (typically greater than one inch for the stopcock valves 120, 140 and greater than two inches in the maximum dimension for the rotary valves 230) relative to the overall desired system size. In particular, their size is large for typical implantable drug-delivery systems, and also for drug-delivery systems mounted on small lab animals typically used for preliminary animal studies. In addition to these large physical dimensions, stopcock valves have relatively large internal fluid volumes (e.g., 100 microliters or greater, including fitting volumes), which is generally undesirable when the total fluid volume of the system is desired to be small. Typical Luer fittings for stopcock valves are designed to mate to similarly sized (i.e., not microscale) fluidic components, and thus also add considerably to system size and internal fluid volume.

As a result, there is a need for both a capacitive element and/or a valve system that is small enough to fit within a microfluidic system, such as an implantable drug-delivery system, while still being capable of performing fluid control functions with sufficient reliability and efficiency.

SUMMARY OF THE INVENTION

In various embodiments, the present invention features compliant membrane-based microfluidic structures that are capable of providing capacitive fluidic control and/or valve control functions for microfluidic systems. The present invention may, for example, be used in drug-delivery systems, including those used for the controlled delivery of drugs to the cochlea or another appropriate target. Use of the present invention is not, however, limited to such systems. Rather, the compliant membrane-based capacitive elements and/or valve elements described herein may be used in any flow system, such as, for example, in systems where positive-displacement pumping is to be converted to reciprocating flow. Examples of other contexts in which the compliant membrane-based capacitive elements and/or valve elements may be used include mixing devices, chemical or biological reactors, diagnostic devices, and hydraulic actuators.

In the drug-delivery context, the present invention may be employed when it is beneficial to apply drugs to a specific bodily fluid. An example is in drug delivery to the inner ear, where drugs are administered directly to the perilymph without having to penetrate surrounding tissue. Additional exemplary applications include those where flow and pressure regulation may be required in microfluidic systems. In particular, systems that use oscillatory pumps having both alternating and constant components to their outputs may be improved by the addition of the compliant membrane-based capacitive elements described herein, which reduce the undesired alternating component of the pump output.

In addition, the structures described herein may have application in drug-delivery developments that use externally mounted components on lab animals, in particular because the size and simplicity of the structures described herein minimize the stress on the animal undergoing tests. Additional exemplary applications include those where sample loading, venting, pressure relief, and sample routing are used in microfluidic systems.

In general, in one aspect, the invention features a capacitive element for a microfluidic device. The capacitive element includes a substrate defining a flow-control cavity and a compliant membrane, surrounding at least a portion of the flow-control cavity, for capacitively regulating fluid flow through the flow-control cavity. The capacitive element also includes a bypass structure for allowing the fluid to flow through the flow-control cavity when the compliant membrane is in a collapsed position.

In various embodiments, the substrate includes a plurality of layers, one of which may include a laminated plastic. For its part, the compliant membrane may be a single-layered structure, a multi-layered structure, and/or a composite structure. The compliant membrane may include a polymer and may also include a layer exhibiting a low vapor and/or gas permeability. The capacitive element may also include an external fluid connection element, which may itself include fine-bore tubing.

In one embodiment, the capacitive element includes a displacement element, which may be manually actuable. The displacement element may limit the outward displacement of the compliant membrane away from the flow-control cavity. In one embodiment, the displacement element is a threaded element. In such a case, the substrate may include a plate with a threaded hole formed therethrough, and the displacement element may be positioned in the threaded hole.

In general, in another aspect, the invention features a microfluidic device that includes a discharge line, a pump for discharging and retracting fluid through the discharge line, and a capacitive element for modifying fluid flow through the discharge line. The capacitive element may include a compliant membrane that surrounds at least a portion of a cavity formed in the capacitive element.

In various embodiments, the capacitive element also includes a bypass structure for allowing fluid to flow through the capacitive element when the compliant membrane is in a collapsed position. The capacitive element may also include a displacement-limiting element for limiting a displacement of the compliant membrane. In various embodiments, the microfluidic device, which may be a reciprocating drug delivery device for regulating a drug dosage delivered to a patient, includes a valve manifold.

In general, in yet another aspect, the invention features a microfluidic valve system. The microfluidic valve system includes a substrate having first and second channels embedded therein, a valve seat in fluid communication with the first and second channels, a compliant membrane, and a mechanically actuable displacement element. The displacement element may apply a mechanical force to the compliant membrane to bring the compliant membrane into sealable contact with the valve seat, thereby closing the valve system.

In various embodiments, the substrate includes a plate with a threaded hole formed therethrough, and the displacement element is positioned in the threaded hole. The displacement element may be manually actuable, and may be a threaded element or a bistable spring-loaded element. The microfluidic valve system may also include an external fluid connection element having fine-bore tubing.

In general, in still another aspect, the invention features a method of controlling fluid flow within a microfluidic device. The method includes passing fluid through a microfluidic device comprising a compliant membrane and a bypass channel, and capacitively displacing at least a portion of the compliant membrane to control a rate of fluid flow through the microfluidic device. The method may also include limiting an outward displacement of the compliant membrane away from the flow-control cavity.

These and other objects, along with advantages and features of the present invention herein disclosed, will become apparent through reference to the following description, the accompanying drawings, and the claims. Furthermore, it is to be understood that the features of the various embodiments described herein are not mutually exclusive and can exist in various combinations and permutations.

BRIEF DESCRIPTION OF THE DRAWINGS

The foregoing and other objects, aspects, features, and advantages of the invention will become more apparent and may be better understood by referring to the following description taken in conjunction with the accompanying drawings, in which.

DESCRIPTION

In various embodiments, the present invention features compliant membrane-based microfluidic structures that are capable of providing capacitive fluidic control and/or valve control functions in microfluidic systems. These capacitive fluidic control and/or valve control structures may be used, for example, in conjunction with the microfluidic devices, systems, and methods described in U.S. Ser. Nos. 11/046,540, 11/169,211, and 11/503,450, the disclosures of which are hereby incorporated herein by reference in their entireties.

Figure 3A:
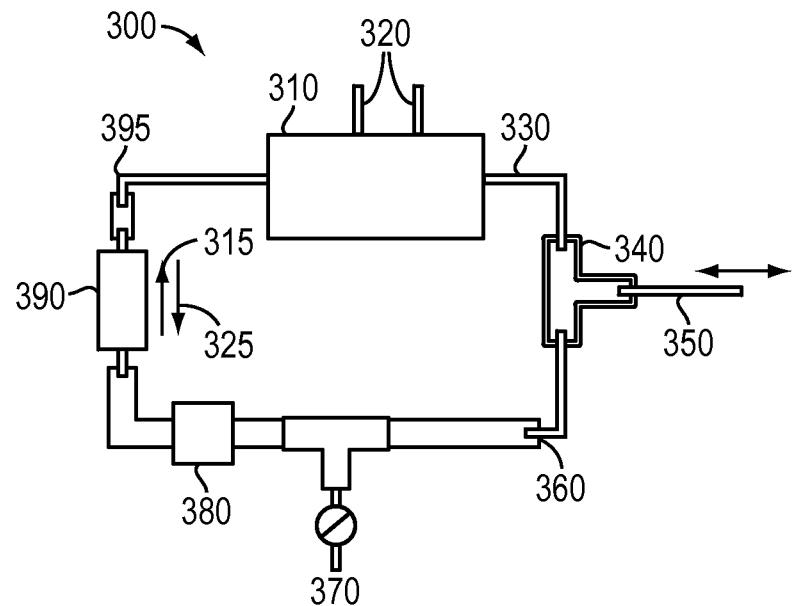
FIG. 3A is a schematic view of a microfluidic system with valves set for loop filling, in accordance with one embodiment of the invention.
Figure 3B:
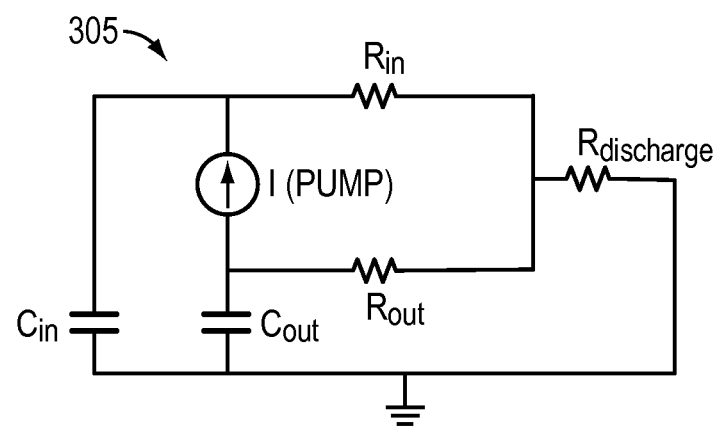
FIG. 3B is a schematic circuit representation of the microfluidic system of FIG. 3A.

In one embodiment, the present invention uses a compliant membrane-based structure, rather than tubing, as a fluidic capacitive element. FIG. 3A depicts an exemplary microfluidic system 300, which serves to allow transient pulsed flow through a discharge line 350, while FIG. 3B depicts an equivalent circuit representation 305 for the microfluidic system 300.

More particularly, as depicted in FIG. 3A, the microfluidic system 300 may include a valve manifold 310 connected to injection lines 320. The valve manifold 310 may include a compliant membrane-based valve structure, for example as described herein with reference to FIGS. 7A-7C. In one embodiment, the valve manifold 310 is connected through rigid tubing 330 to a discharge manifold 340, which is connected to a discharge line 350 for delivering fluid to, and possibly receiving fluid from, a target area of a body, such as a cochlea. The discharge manifold 340 may also be connected to a second rigid tubing section 360, which may itself be connected to a vent valve 370. In an alternative embodiment, the vent valve 370 is absent from the microfluidic system 300. When present, the vent valve 370 may be connected to a compliant membrane-based capacitive element 380, such as, for example, the capacitive elements described herein with reference to FIGS. 4A-4C and 5. The compliant membrane-based capacitive element 380 may provide the required capacitive fluidic control to the system 300, as described herein. In one embodiment, the capacitive element 380 is attached to a pump 390, which is then attached through a length of tubing 395 to the valve manifold 310, thereby completing the fluid loop. In alternative embodiments, the configuration of elements in the fluid loop may be differently arranged. In addition, the fluid loop may include further elements, or exclude some of the elements depicted in FIG. 3A, as appropriate.

The capacitance of the capacitive element 380 is typically an important factor in setting the behavior of the flow characteristics, i.e., how rapidly fluid is discharged and retracted through the discharge line 350. For example, if the capacitance is increased, the discharge rate slows down, and vice-versa. In addition, in one embodiment, if the direction of pulsed flow is that indicated by arrow 315 in FIG. 3A, fluid will be first discharged rapidly through the discharge line 350 and then slowly retracted (i.e., pulled back into the loop). Alternatively, if the direction of pulsed flow is that indicated by arrow 325 in FIG. 3A, fluid will be first drawn rapidly into the system 300 and then slowly discharged. These characteristics may be advantageous in delivering a drug to a target area, and/or in mixing the drug with a body fluid drawn into the fluidic system 300 through the discharge line 350.

Using a compliant membrane-based structure, rather than tubing, as the fluidic capacitive element 380 in the microfluidic system 300 provides several advantages. For example, the compliant membrane-based capacitive element 380 may be easily integrated onto a single substrate with other microfluidic elements, thus reducing the size of the system 300 and easing the manufacture of the system 300. In addition, in one embodiment, connecting the compliant membrane-based capacitive element 380 to the other microfluidic elements does not require the use of macro-scale connectors. Thus, leakage through, and dead volume in, these elements are avoided. Moreover, by using thin, compliant layers for the membrane of the capacitive element 380, large capacitance values may be achieved while the total element volume remains small. As previously described, this is typically not the case when tubing is used.

In addition, because the compliant membrane-based capacitive element 380 may be manufactured to have a small surface area, and because a variety of materials having low intrinsic gas and/or vapor permeabilities are available to be used as membranes, the compliant membrane-based capacitive element 380 may have an extremely low permeability to gas and/or vapor. In another embodiment, by using a displacement-limiting element, for example a screw, the capacitance of the compliant membrane-based capacitive element 380 may be altered or adjusted to any desired value within a range of values.

In greater detail, as described below with reference to FIGS. 4A-4D and 5, one embodiment of the invention features a microfabricated membrane that forms at least one wall, or partial wall, of a cavity. In one embodiment, the membrane has sufficient compliance such that when fluid pressure in the cavity is changed, the cavity volume changes due to the displacement of at least a portion of the membrane. The membrane may be directly integrated with other microfluidic structures such as channels, pumps, and valves in the same base substrate. No tubing or bellows structure is required. In addition, in one embodiment, the compliant membrane-based capacitive element 380 of the present invention has a capacitance value that may be altered during in-use operation, as desired. For example, in one embodiment, a screw or other displacement/blocking element may be positioned above the membrane, with its distance relative to the relaxed position of the membrane capable of being altered to limit the maximum displacement of the membrane as the capacitive cavity is pressurized.

Figure 4A:
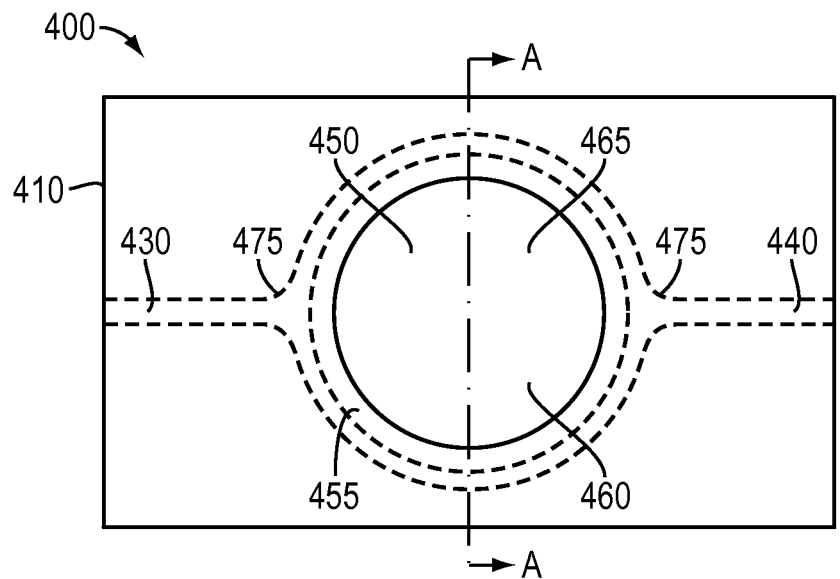
FIG. 4A is a schematic top view of a compliant membrane-based capacitive element, in accordance with one embodiment of the invention.

FIG. 4A depicts a top view of a compliant membrane-based capacitive element 400 embedded within a substrate 410 in accordance with one embodiment of the invention. The capacitive element 400 includes a fluid-control cavity 420 with a first channel 430 and a second channel 440 entering the cavity 420 at opposite ends. Alternatively, the first channel 430 and second channel 440 may connect to the cavity 420 at a suitable angle to one another, depending on the application. In addition, more than two channels may be connected to the cavity 420. The cavity may be substantially cylindrical (as depicted in FIGS. 4A-4D), or be of another appropriate shape, such as an oval, a spherical-shape, a cubic-shape, or other appropriate geometry.

Figure 4B:
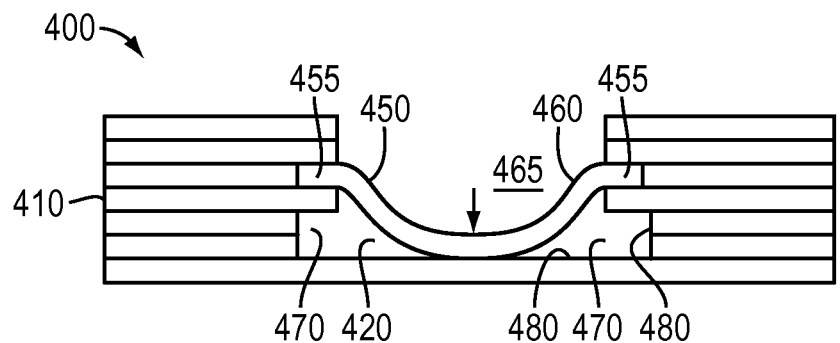
FIG. 4B is a cross-sectional view of the compliant membrane-based capacitive element of FIG. 4A along the line A-A, when the capacitive element is in a closed configuration.

In one embodiment, the upper surface of the cavity 420 is bounded by a compliant membrane 450 that is clamped around its outer edge 455 so that it forms a sealed wall of the cavity 420 while being free to expand into or out of the cavity 420 at a central portion 460. As illustrated in FIG. 4B, an expansion hole 465 may be formed within the substrate 410 directly above the membrane 450 to provide an open area for the central portion 460 of the membrane 450 to expand into as it extends outwardly from the cavity 420. In an alternative embodiment, the membrane 450 may be located at the outer layer of the substrate 410, thus allowing it to extend outwardly into the surrounding area without the need for the expansion hole 465.

In one embodiment, by creating a pressure differential between the pressure within the cavity 420 and the pressure within the expansion hole 465, the compliant membrane 450 may move into or out of the cavity 420, thus increasing or decreasing the volume of the cavity 420. For example, if the pressure within the cavity 420 is less than that in the expansion hole 465, the central portion 460 of the membrane 450 will be forced down into the cavity 420, thus reducing the volume of the cavity 420 and thereby restricting the fluid flow therethrough, as depicted in FIG. 4B.

Figure 4C:
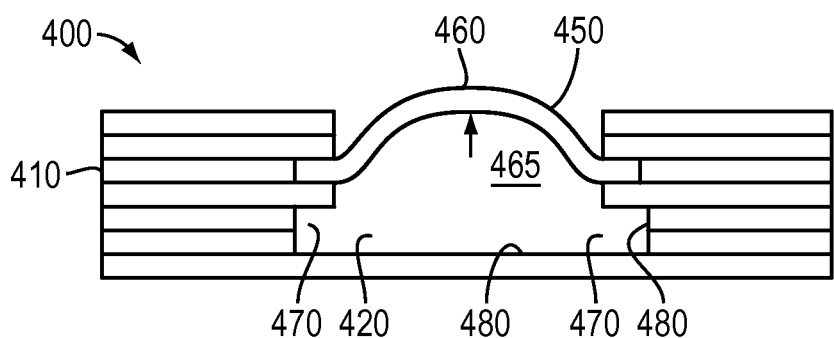
FIG. 4C is a cross-sectional view of the compliant membrane-based capacitive element of FIG. 4A along the line A-A, when the capacitive element is in an open configuration.

Alternatively, if the pressure within the cavity 420 is greater than that in the expansion hole 465, the central portion 460 of the membrane 450 will be forced outwardly into the expansion hole 465, thus increasing the volume of the cavity 420 and thereby reducing the restriction to fluid flow, as depicted in FIG. 4C.

As a result, in one embodiment, the compliant membrane-based capacitive element 400 promotes and/or restricts fluid flow by changing the volume of the cavity 420. The compliant membrane-based capacitive element 400 may also increase and/or decrease the fluid storage volume of the cavity 420, and thereby of the associated microfluidic device, by moving the compliant membrane 450 into or out of the cavity 420. In addition, by allowing the compliant membrane 450 to move in response to pressure changes within the fluid flow, the compliant membrane-based capacitive element 400 may also provide a capacitive function. More specifically, the capacitive element 400 may provide a frequency response filtering of time-varying flow and/or pressure sources within the microfluidic device, thereby damping out rapid changes in flow or pressure occurring throughout the fluid flow cycle.

The pressure differential between the cavity 420 and the expansion hole 465 may be created, for example, by properties of the fluid flow itself as it is pumped through the microfluidic system. For example, in microfluidic systems for delivering one or more drugs to the cochlea, such as the system 300 depicted in FIG. 3A, the pressure within the cavity 420 will vary as the microfluidic pump 390 discharges and retracts fluid through the discharge line 350 in a pulsed flow. As a result, the central portion 460 of the membrane 450 will be forced inward toward the cavity 420 and outward into the expansion hole 465 as the pressure within the cavity 420 varies during the pulsed fluid-flow cycle, thereby providing a capacitive control for the fluid flow. This may be advantageous, for example, in embodiments where the desired fluid flow rate is lower in amplitude and extended in time downstream of the capacitive element 400 relative to the pulsatile flow rate through a pump upstream of the capacitive element 400.

In one embodiment, the compliant membrane-based capacitive element 400 performs frequency response filtering of time-varying flow or pressure sources. For example, the capacitive element 400 may act as a low pass filter for fluid flow driven by a rapid-pulse pump. In particular, in one embodiment, the compliant membrane-based capacitive element 400 does not have any effect on a steady state flow rate, such as, for example, a mean constant-velocity unidirectional flow (analogous to a DC electrical current in an electrical system). However, in such an embodiment, the compliant membrane-based capacitive element 400 may have a substantial effect on a transient flow rate (i.e., a time-varying flow). As a result, the compliant membrane-based capacitive element 400 may provide pressure control for a fluid flowing within a microfluidic device.

In some cases, for example those where it is desirable to reduce the pressure inside the cavity 420 to a value below that of the pressure outside the cavity 420 (i.e., a negative pressure differential), the capacitive membrane element 400 may be configured so that fluid continues to flow through the element 400 even in the event of a partial or substantially full collapse of the membrane 450 into the cavity 420. To achieve this, one or more bypass channels 470, examples of which are illustrated FIGS. 4A-4D, may be incorporated into the capacitive element 400. In addition, as part of the capacitive cavity structure, the inlet and/or outlet channels 430, 440 may be fashioned with chamfers 475, which may, for example, prevent the trapping of unwanted gas bubbles inside the cavity 420 when fluid is flowing through the cavity 420.

Figure 4D:
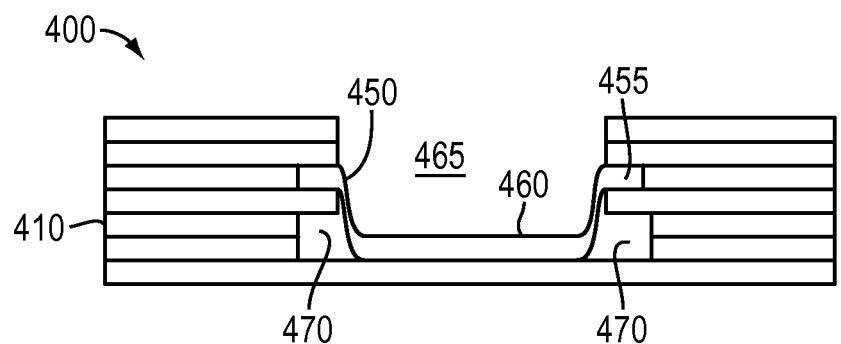
FIG. 4D is a cross-sectional view of the compliant membrane-based capacitive element of FIG. 4A along the line A-A, when the capacitive element is in a collapsed position.
Figure 5:
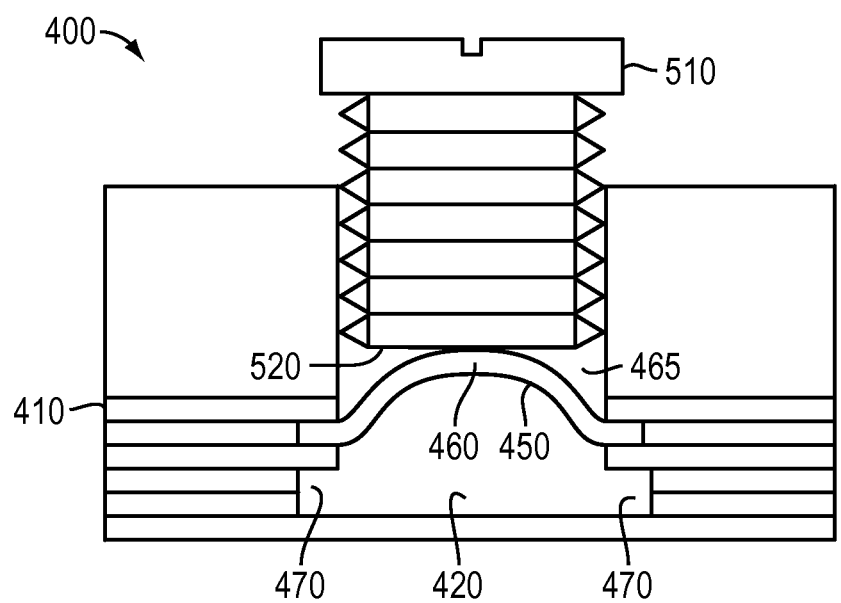
FIG. 5 is a cross-sectional view of a compliant membrane-based capacitive element and displacement element, in accordance with one embodiment of the invention.

For example, FIG. 4D depicts a capacitive element 400 in which the membrane 450 is fully collapsed into the cavity 420. In this embodiment, the bypass channels 470 act as fluid flow channels to prevent a total, or substantially total, blocking of fluid flow through the cavity 420. This may be useful in, for example, implantable drug delivery devices where fluid flow, and therefore drug delivery, is required to be maintained even in the event of a membrane 450 collapse. The bypass channels 470 may also serve to prevent large fluid pressure changes in the system and thus prevent excessive stresses being applied to components of a microfluidic device, such as a pump of a drug delivery device.

The membrane 450 may be of the same material (as depicted in FIG. 4C) or of a different material (as depicted in FIG. 4B) from that of the other wall(s) 480 of the cavity 420. In addition, the substrate 410 may be manufactured from a single layer or a plurality of layers of the same or different materials. The cavity 420 and channels 430, 440 may be formed in the substrate 410 in accordance with any appropriate manufacturing method, such as, for example, etching, machining, or laser ablation.

In one embodiment, the wall(s) of the cavity 420 (other than the membrane 450) are made from the same material(s) as the substrate 410. In an alternative embodiment, a separate material may be embedded within the cavity 420 to create an impermeable wall, or other appropriate structure, for the cavity 420.

For its part, the membrane 450 may be composed of a single material or layer, or of multiple materials, layers, and/or composites. In addition, some or all of the membrane 450 layers may act as a barrier to vapor and/or gas. As an example, a vapor-permeable polymer material may be combined with a thin layer of barrier metal to form a composite membrane 450 that is both compliant and also resistant to moisture, gas, and/or vapor transport through it. Such low-permeability structures may be desirable in applications where the microfluidic system is in use for long periods of time and is not refilled or reloaded with fluid.

The thickness, diameter, and material stiffness of the membrane 450 may also be chosen to achieve a desired capacitance value. In one embodiment, the membrane 450 has sufficient compliance such that when fluid pressure in the cavity 420 is changed, the volume of the cavity 420 changes due to displacement of the membrane 450. In one embodiment, the capacitance has units of volume per unit pressure differential, e.g., microliters/Pascal. As described herein, the compliant membrane-based capacitive element 400 may be directly integrated with other microfluidic structures such as channels, pumps, and valves in the same base substrate 410, or within a number of connected substrates, as required.

The capacitive properties of the capacitive element 400 may be varied by limiting the displacement of the central portion 460 of the membrane 450. In one embodiment, the capacitive element 400 is used together with a displacement element that is adapted to alter or adjust, in-use, the capacitance of the capacitive element 400 to any value within a range of values by limiting the displacement of the central portion 460 of the membrane 450. This displacement element may be actuated manually. Alternatively, the displacement element may be actuated automatically, either by a signal from a remote location or in response to a condition of the system. The displacement element may be a mechanical element, a magnetic element, a hydraulic element, a solenoid, an electrical element, or combinations thereof. For example, in the embodiment depicted in FIG. 5, the displacement element is a threaded element 510 (e.g., a screw) that is positioned above the central portion 460 of the membrane 450 within the expansion hole 465. By moving the threaded displacement element 510 up and down within the expansion hole 465, the distance of a distal face 520 of the threaded displacement element 510 relative to a relaxed position of the central portion 460 of the membrane 450 (i.e., when the central portion 460 of the membrane 450 is not displaced in either direction) is altered, as is the maximum distance the membrane 450 may be displaced and thus the capacitance of the capacitive element 400. The shape of the distal face 520 of the displacement element 510 may also be chosen to give different capacitance vs. screw displacement functions.

The displacement element 510 may additionally be used to force the central portion 460 of the membrane 450 down into the cavity 420, thereby reducing the volume of the cavity 420 and, as a consequence, the fluid flow therethrough. In one embodiment, the cavity 420 may be configured without bypass channels 470, thus allowing the central portion 460 of the membrane 450 to seal the cavity 420 upon full displacement of the displacement element 510. In such a case, the capacitive element 400 acts as a valve element.

As described, embodiments of the present invention that use the compliant membranes 450 as capacitive elements 400 provide several advantages and have many applications. For example, compliant membrane-based capacitive elements 400 may be used to regulate drug dose in a reciprocating drug delivery device. In addition, the built-in bypass structures 470 provide a safety mechanism against the complete blocking of fluid flow in the event of a structural collapse of the membrane 450.

Figure 1A:
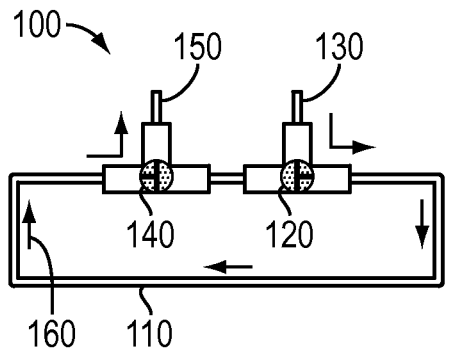
FIG. 1A is a schematic view of prior art stopcock valves set in a manifold loading position.
Figure 1B:
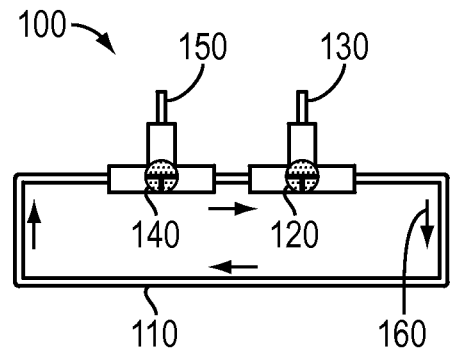
FIG. 1B is a schematic view of the stopcock valves of FIG. 1A set for loop circulation.
Figure 2A:
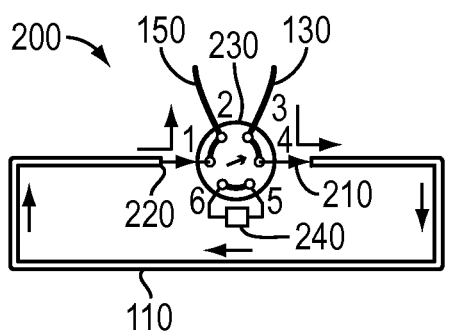
FIG. 2A is a schematic view of a prior art rotary valve set in a manifold loading position.
Figure 2B:
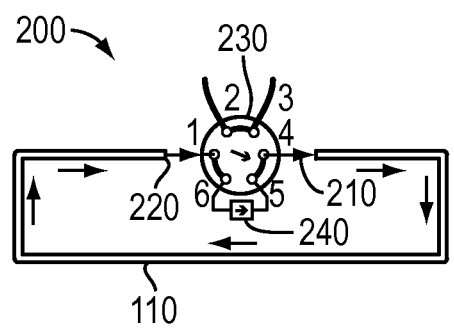
FIG. 2B is a schematic view of the rotary valve of FIG. 2A set for loop circulation.

Additional embodiments of the present invention relate to the use of valves in a microfluidic system, such as a drug-delivery device. The valves may be used for filling or venting a microfluidic system, such as the microfluidic system 100 depicted in FIGS. 1A and 1B. For example, a valve system may be used with the manifold 110 while filling the recirculation loop of the microfluidic system 100.

Figure 6A:
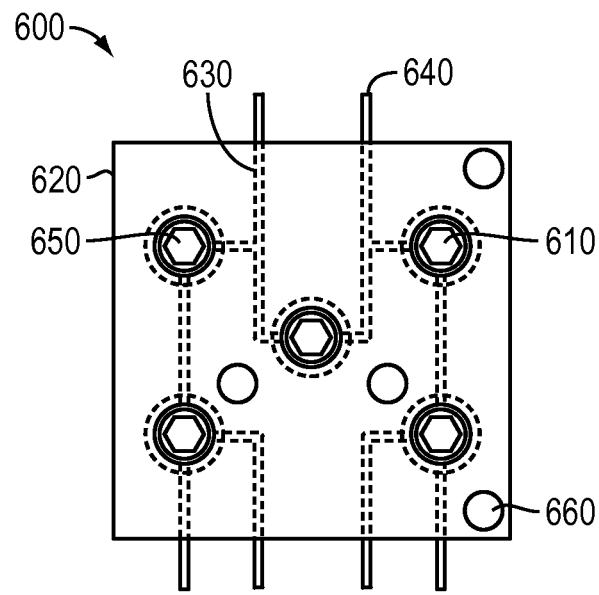
FIG. 6A is a schematic top view of a five-valve manifold with an integrated channel network, in accordance with one embodiment of the invention.
Figure 6B:
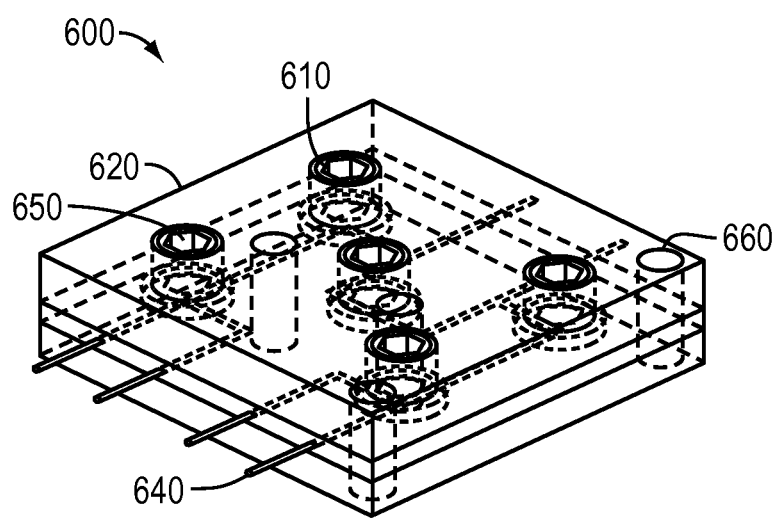
FIG. 6B is a schematic perspective view of the five-valve manifold of FIG. 6A.

Referring to FIGS. 6A and 6B, the present invention, in one embodiment, features a valve system 600 that contains one or more valves 610 on a single planar substrate 620. The substrate 620 may define fluidic channels 630 that connect the valves 620 to each other and to external tubing connections 640, as appropriate for the desired function. The valve system 600 is, in one embodiment, incorporated into a microfluidic device, such as, for example, the microfluidic device 100 depicted in FIGS. 1A-1B, and is used to regulate flows therein. For example, a particular valve 610 of the valve system 600 may be set in a partially open configuration. As described below, this setting may be variable, thereby providing a variable resistance to fluid flow through the valve 610. In contrast, many prior valve systems may typically only be either fully open or fully closed.

The substrate 620 may also contain built-in fine-bore tubing mated to appropriate fluidic channels and be used to fit to additional components in a microfluidic system or manifold. Other appropriate means of mating components may also be utilized. The substrate 620 may also contain other microfluidic components, such as, but not limited to, additional compliant structures, fluidic capacitors, electronically actuated valves and/or pumps, mixing chambers, and reservoirs.

FIGS. 6A and 6B depict a valve system 600 on a substrate 620 that incorporates five valves 610. In alternative embodiments, a greater and/or lesser number of valves 610 are incorporated into the valve system 600 in any appropriate configuration. In one embodiment, valve screws 650 for the valves 610 are #0-80 hex-head set screws. Alternatively, other appropriate screw elements may be employed. The additional holes 660 depicted in FIGS. 6A and 6B may be used for other purposes, such as, but not limited to, mounting of the system 600. In addition, the top plate of the valve system 600 may be partially transparent to provide clarity.

Figure 7A:
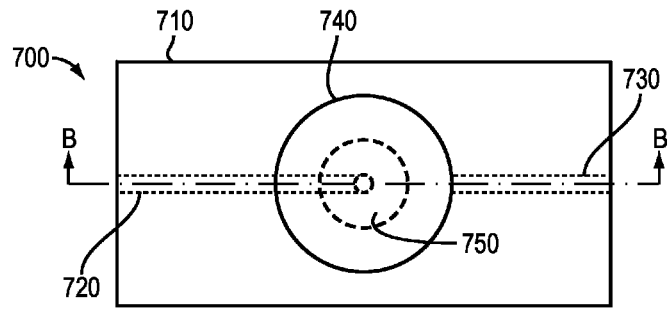
FIG. 7A is a schematic plan view of a compliant membrane-based valve structure, in accordance with one embodiment of the invention.
Figure 7B:
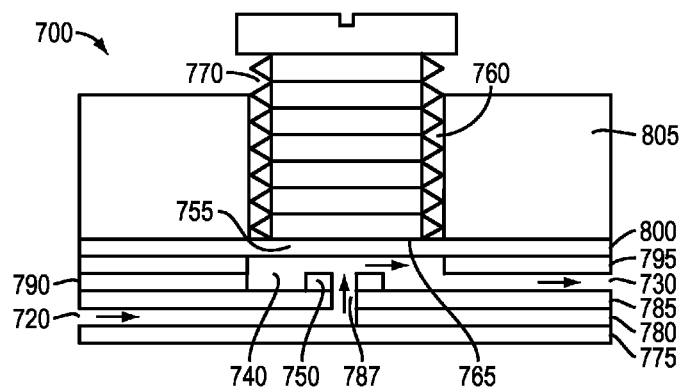
FIG. 7B is a cross-sectional side view of the compliant membrane-based valve structure of FIG. 7A along the line B-B, when the valve structure is in an open configuration.
Figure 7C:
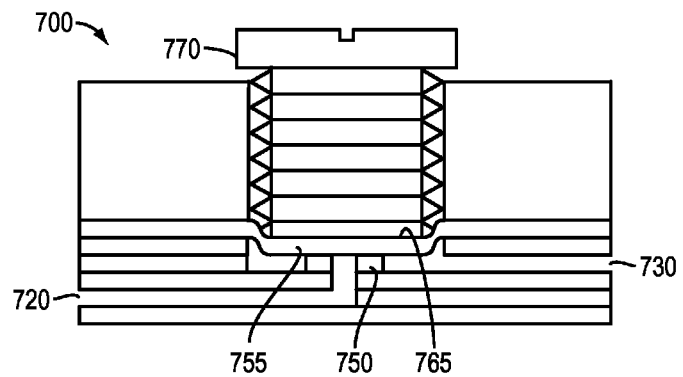
FIG. 7C is a cross-sectional side view of the compliant membrane-based valve structure of FIG. 7A along the line B-B, when the valve structure is in a closed configuration.

FIGS. 7A-7C depict, in accordance with one embodiment of the invention, an exemplary valve 700 that may be used in the valve system 600 described above. In this embodiment, the compliant membrane-based valve structure 700 includes a substrate 710 that defines a first channel 720, a second channel 730, and a cavity 740 therebetween. As illustrated in FIG. 7B, the first channel 720, second channel 730, and cavity 740 may be in fluid communication with one another. In an alternative embodiment, additional inlet and/or outlet channels may be placed in fluid communication with the cavity 740.

In one embodiment, a valve seat 750 is included in the cavity 740. A compliant membrane 755 forms at least one wall to the cavity 740. The membrane 755 may be a separate element embedded within the substrate 710 and held in place by a clamping region at its outer edge, or be an integral part of one or more layers of the substrate 710.

The substrate 710 may also include a threaded hole 760 for holding a threaded displacement element 770. The threaded displacement element 770 may be configured such that its distal end 765 abuts, in operation, a central portion of the membrane 755. The displacement element 770 may then be used to push the central portion of the membrane 755 against the valve seat 750, thereby sealing the cavity 740 and preventing fluid flow between the first channel 720 and the second channel 730. In an alternative embodiment, the valve seat 750 is not employed. In such a case, the membrane 755 may be forced directly against a bottom surface of the cavity 740 in order to seal the cavity 740 and prevent fluid flow.

In another embodiment, the threaded displacement element 770 is threaded only partially downward into the cavity 740 such that the membrane 755 reduces the volume of the cavity 740 and reduces the fluid flow therethrough, without completely blocking the flow. As a result, the valve system 700 may be used to control the rate of fluid-flow therethrough, in addition to completely preventing flow. In still another embodiment, the valve system 700 includes one or more bypass channels that allow a limited flow therethrough even if the membrane 755 is fully sealed against the valve seat 750.

In one embodiment, the threaded displacement element 770 is retracted away from the membrane 755, either completely or by a limited distance, such that the compliant membrane 755 and cavity 740 act as a compliant membrane-based capacitive element, as described above.

The displacement element 770 may be a mechanically actuable displacement element that is manually actuated and/or automatically actuated, for example through a control system in response to a fluid flow condition. For example, the displacement element 770 may be a mechanically actuable element that is adapted to provide a mechanical force directly to at least a portion of the membrane 755 upon actuation. Examples of mechanically actuable displacement elements 770 include, but are not limited to, one or more threaded elements, spring elements, bistable spring-loaded elements, rotating cam elements, pushing rod elements, hydraulic elements, and/or other appropriate mechanical force providing elements.

In one embodiment, the displacement element 770 is a standard metal screw, such as, for example, a #0-80 hex head screw, mounted in a tapped hole in an upper rigid layer of the structure. Alternatively, the screw may be made from a plastic, such as nylon, or another appropriate material. In other embodiments, the displacement element 770 has two stable states, and has a structure similar to that of the click action or press action mechanism of a retractable ball-point pen (i.e., a bistable spring-loaded device). The states may be switched via either rotation or axial displacement (e.g., pushing) of the displacement element 770.

As mentioned, the mechanically actuable displacement element 770 may be manually actuated. For example, in embodiments where the valve system 700 is accessible to a user, a threaded displacement element 770 may be actuated through insertion and rotation of a screwdriver or other actuation element by a user, or a bistable "click-action" type displacement element 770 may be pushed by the user. In embodiments where the valve system 700 is implanted in a patient and inaccessible to a user, a control device may be mechanically coupled to the mechanically actuable displacement element 770 and may apply a mechanical force thereto to actuate the displacement element 770. This control device may itself be a mechanical, electromagnetic, hydraulic, or other appropriate actuation device, and may mechanically actuate the displacement element 770 in response to a fluid flow condition and/or a control input from a remote location.

In one embodiment of the invention, the bottom face 765 of the displacement element 770 has a ring-shaped boss with a radius either substantially identical to, or similar in value to, the valve seat 750 radius, and thus preferentially applies pressure to the membrane 755 on the valve seat 750 area.

Any appropriate method of manufacturing the multi-layered substrate 710 may be used. For example, in one embodiment, the first channel 720 is formed by a through-cut or partial-depth cut of a single layer 780 of thin bondable polymer sheet. The bottom of the channel 720 may be either in the same layer 780 or formed by another sheet 775 of polymer bonded to it. A different polymer sheet 785 may provide the top of the first channel 720 and may be patterned with a through-hole 787 that connects the channel 720 to the valve cavity 740. A further polymer sheet 790 may be patterned to form the valve seat 750, the lower portion of the valve cavity 740, and, optionally, a second channel 730. The valve seat 750 may be a protruding ring, (i.e., a ring-shaped boss element) or any other appropriately shaped seating element. The ring may be axially aligned with the through hole 787 in layer 785.

In order to create and facilitate convenient assembly of the valve seat 750, layer 785 and layer 790 may be either bonded together before patterning (for example by etching, machining, ablation, and/or other appropriate patterning techniques), or a single layer may be substituted for both. In either case, a partial-depth cut may define the outer diameter of the valve seat 750 and a through-cut may define the inner diameter of the seat 750 and flow access to the first channel 720.

The second channel 730 may also be formed from either a partial-depth or through-cut pattern in the layer 790. A further layer 795 may be cut to form the upper part of the valve chamber and, optionally, the second channel 730 or a portion thereof. An additional layer 800 may form the valve membrane 755. Finally, an additional layer of a material 805 such as, but not limited to, aluminum or other appropriate metal, plastic, or polymer, with aligned holes for the displacement elements 770, may be attached to the membrane layer 800. The layer 805 may be thicker than one or more of the other layers and/or be substantially rigid.

In an alternative embodiment, layer 790 is not used. In this case, when the displacement element 770 is in the open position (i.e., displaced away from the membrane 755), the membrane 755 may still be in contact with the valve seat 750, and thus significant fluid pressure will be required to displace the membrane 755 and allow flow. In this case, it is desirable for no bonding material or adhesive to be present on the valve seat 750 during component fabrication.

The polymer sheets 775, 780, 785, 790, 795, 800, and/or other appropriate layers constituting the substrate 710, may be prefabricated with thin layers of adhesive on one or both of their sides. Optionally, stand-alone layers of adhesive may be patterned and aligned with the polymer sheets 775, 780, 785, 790, 795, 800 and stacked prior to the bonding step(s). In one embodiment, the bonding of the layers of the substrate 710 may include a high-temperature, high-pressure adhesive-bonding and curing step.

As described, the compliant membrane valve systems 700 provide several advantages and have many applications. For example, by using a screw or other manually-actuated axial displacement element 770 to displace the membrane 755, a simple means of manually or automatically controlling fluid flow within a microfluidic system is achieved. In addition, compliant membrane valve systems 700 may be configured to provide both recirculating flow and/or loading and venting flow for a microfluidic system, such as the microfluidic system of FIG. 3A.

In some embodiments of the invention, the compliant membrane-based fluidic control elements are very small. For example, the five-valve manifold 600 depicted in FIGS. 6A and 6B may have a size of approximately 1 cm by 1 cm by 3 mm, or less. In addition, the valves may be integrated on a single substrate with other microfluidic elements and, as such, connecting a valve to these other elements avoids the need for macroscale connectors. Thus, leakage through, and dead volume in, these elements are avoided. Moreover, because of the large number of valves that may be implemented within a small volume, a wide variety of fluid routing functions may be easily achieved. In contrast, prior valve systems known in the art typically become bulky and unwieldy as the number of valves becomes large.

As described herein, a microfluidic device that includes a compliant membrane may be used to provide both capacitive fluid control and a valve function for a fluidic system. In addition, a plurality of microfluidic devices, incorporating various functions of the invention described herein, may be used within a microfluidic system, as required. For example, a microfluidic system may include one or more compliant membrane-based capacitive elements and/or one or more compliant membrane-based valves.

Having described certain embodiments of the invention, it will be apparent to those of ordinary skill in the art that other embodiments incorporating the concepts disclosed herein may be used without departing from the spirit and scope of the invention. Accordingly, the described embodiments are to be considered in all respects as only illustrative and not restrictive.

What is claimed is:

1. A capacitive element for a microfluidic device, comprising:
   a substrate including a channel within the substrate defining a flow-control cavity and a bypass structure, wherein the channel includes a bottom, side walls, and a partial ceiling, wherein the partial ceiling extends over at least a portion of the channel;
   a compliant membrane, surrounding at least a portion of the flow-control cavity, for capacitively regulating fluid flow through the flow-control cavity;
   wherein the bypass structure is separated from the membrane by the partial ceiling and is configured to allow the fluid to flow through the flow-control cavity when the compliant membrane is collapsed into the flow-control cavity; and
   a displacement-limiting element, coupled to the substrate and uncoupled from the compliant membrane, for limiting the outward displacement of the compliant membrane away from the flow-control cavity.

2. The capacitive element of claim 1, wherein the substrate comprises a plurality of layers.

3. The capacitive element of claim 2, wherein at least one of the plurality of layers comprises a laminated plastic.

4. The capacitive element of claim 1, wherein the compliant membrane comprises at least one of a multi-layered structure or a composite structure.

5. The capacitive element of claim 1, wherein the compliant membrane comprises a polymer.

6. The capacitive element of claim 1, wherein the compliant membrane comprises a layer exhibiting at least one of a low vapor permeability or a low gas permeability.

7. The capacitive element of claim 1 further comprising an external fluid connection element having fine-bore tubing.

8. The capacitive element of claim 1, wherein the displacement-limiting element comprises a threaded element.

9. The capacitive element of claim 8, wherein the substrate comprises a plate with a threaded hole formed therethrough, and wherein the displacement-limiting element is positioned in the threaded hole.

10. The capacitive element of claim 1, wherein the displacement-limiting element is manually actuable.

11. A microfluidic device, comprising:
    a discharge line;
    a pump for discharging and retracting fluid through the discharge line; and
    a capacitive element for modifying fluid flow through the discharge line, the capacitive element comprising:
       a compliant membrane that surrounds at least a portion of a channel formed within a substrate of the capacitive element, the channel including a flow-control cavity and a bypass structure;
       wherein the channel includes a bottom, side walls, and a partial ceiling extending over at least a portion of the channel, and wherein the bypass structure is separated from the membrane by the partial ceiling and is configured to allow the fluid to flow through the flow-control cavity when the compliant membrane is collapsed into the flow-control cavity; and
       an adjustable displacement-limiting element, coupled to the substrate of the capacitive element and uncoupled from the compliant membrane, for limiting an outward displacement of the compliant membrane away from the cavity.

12. The microfluidic device of claim 11 further comprising a valve manifold.

13. The microfluidic device of claim 11, wherein the microfluidic device is a reciprocating drug delivery device for regulating a drug dosage delivered to a patient.

14. A method of controlling fluid flow within a microfluidic device, the method comprising:
    a) passing fluid through a microfluidic device comprising i) a compliant membrane that surrounds at least a portion of a channel formed within a substrate of the microfluidic device, the channel including a flow-control cavity and a bypass structure, ii) wherein the channel includes a bottom, side walls, and a partial ceiling extending over at least a portion of the channel, and wherein the bypass structure is separated from the membrane by the partial ceiling and is configured to allow the fluid to flow through the flow-control cavity when the compliant membrane is collapsed into the flow-control cavity, and iii) a displacement limiting element coupled to the substrate of the microfluidic device and uncoupled from the compliant membrane; and
    b) capacitively displacing at least a portion of the compliant membrane to control a rate of fluid flow through the microfluidic device while limiting an outward displacement of the compliant membrane away from the cavity with the displacement-limiting element.

15. A capacitive element for a microfluidic device, comprising:
    a substrate including a channel within the substrate defining a flow-control cavity and a bypass structure, wherein the channel includes a bottom, side walls, and a partial ceiling, wherein the partial ceiling extends over at least a portion of the channel;
    a compliant membrane, surrounding at least a portion of the flow control cavity, for capacitively regulating fluid flow through the flow-control cavity;
    wherein the bypass structure is separated from the membrane by the partial ceiling and is configured to allow the fluid to flow through the flow control cavity when the compliant membrane is collapsed into the flow-control cavity.

16. The capacitive element of claim 15, wherein the substrate is comprised of a plurality of layers.

17. The capacitive element of claim 16, wherein at least one of the plurality of layers comprises a laminated plastic.

18. The capacitive element of claim 15, wherein the compliant membrane comprises at least one of a multi-layered structure or a composite structure.

19. The capacitive element of claim 15, wherein the compliant membrane comprises a polymer.

20. The capacitive element of claim 15, wherein the compliant membrane comprises a layer exhibiting at least one of a low vapor permeability or a low gas permeability.

21. The capacitive element of claim 15 further comprising an external fluid connection element having fine-bore tubing.

22. A microfluidic device, comprising:
    a discharge line;
    a pump for discharging and retracting fluid through the discharge line; and a capacitive element for modifying fluid flow through the discharge line, the capacitive element comprising:
a compliant membrane that surrounds at least a portion of a channel formed within a substrate of the capacitive element, the channel including a flow-control cavity and a bypass structure; and
wherein the channel includes a bottom, side walls, and a partial ceiling extending over at least a portion of the channel, and wherein the bypass structure is separated from the membrane by the partial ceiling and is configured to allow the fluid to flow through the flow-control cavity when the compliant membrane is collapsed into the flow-control cavity.

23. The microfluidic device of claim 21 further comprising a valve manifold.

24. The microfluidic device of claim 21, wherein the microfluidic device is a reciprocating drug delivery device for regulating a drug dosage delivered to a patient.

25. A method of controlling fluid flow within a microfluidic device, the method comprising:

a) passing fluid through a microfluidic device comprising i) a compliant membrane that surrounds at least a portion of a channel formed within a substrate of the microfluidic device, the channel including a flow-control cavity and a bypass structure, ii) wherein the channel includes a bottom, side walls, and a partial ceiling extending over at least a portion of the channel, and wherein the bypass structure is separated from the membrane by the partial ceiling and is configured to allow the fluid to flow through the flow-control cavity when the compliant membrane is collapsed into the flow-control cavity, and iii) a displacement limiting element coupled to the substrate of the microfluidic device and uncoupled from the compliant membrane; and b) capacitively displacing at least a portion of the compliant membrane to control a rate of fluid flow through the microfluidic device.

* * * * *